US006632244B1

(12) United States Patent
Nigam

(10) Patent No.: US 6,632,244 B1
(45) Date of Patent: Oct. 14, 2003

(54) CORNEAL IMPLANT AND METHOD OF MANUFACTURE

(75) Inventor: Alok Nigam, Trabuco Canyon, CA (US)

(73) Assignee: Anamed, Inc., CA (US)

( * ) Notice: Subject to any disclaimer, the term of this patent is extended or adjusted under 35 U.S.C. 154(b) by 0 days.

(21) Appl. No.: 09/656,059

(22) Filed: Sep. 6, 2000

Related U.S. Application Data

(60) Division of application No. 09/385,103, filed on Aug. 27, 1999, now Pat. No. 6,361,560, which is a continuation-in-part of application No. 09/219,594, filed on Dec. 23, 1998, now Pat. No. 6,102,946.

(51) Int. Cl.[7] ................................................ A61F 2/16
(52) U.S. Cl. ..................................... 623/6.59; 623/6.56
(58) Field of Search ............................... 623/6.11, 6.56, 623/6.59, 6.61

(56) References Cited

U.S. PATENT DOCUMENTS

| | | | |
|---|---|---|---|
| 4,452,235 A | 6/1984 | Reynolds | 128/1 R |
| 4,466,705 A * | 8/1984 | Michelson | 623/5.16 |
| 4,624,669 A | 11/1986 | Grendahl | 623/5 |
| 4,646,720 A | 3/1987 | Peyman | 128/1 R |
| 4,663,358 A | 5/1987 | Hyon et al. | 521/64 |
| 5,098,444 A * | 3/1992 | Feaster | 623/6.36 |
| 5,123,921 A * | 6/1992 | Werblin et al. | 623/4.1 |
| 5,139,518 A | 8/1992 | White | 623/5 |
| 5,244,799 A | 9/1993 | Anderson | 435/240.23 |
| 5,273,750 A | 12/1993 | Homiger et al. | 424/427 |
| 5,300,116 A | 4/1994 | Chirila et al. | 623/5 |
| 5,458,819 A | 10/1995 | Chirila et al. | 264/1.7 |
| 5,713,957 A * | 2/1998 | Steele et al. | 623/5.16 |
| 5,722,971 A | 3/1998 | Peyman | 606/5 |
| 5,800,529 A | 9/1998 | Brauker et al. | 623/11 |
| 5,824,086 A | 10/1998 | Silvestrini | 623/5 |

FOREIGN PATENT DOCUMENTS

| | | |
|---|---|---|
| DE | 32 08 729 | 9/1983 |
| EP | 0 308 077 | 3/1989 |
| EP | 0 420 549 | 4/1991 |
| WO | WO 96 26690 | 9/1996 |
| WO | 9808549 | 3/1998 |
| WO | WO 98 48715 | 11/1998 |
| WO | WO 00 38594 | 7/2000 |

* cited by examiner

Primary Examiner—Corrine McDermott
Assistant Examiner—Hieu Phan
(74) Attorney, Agent, or Firm—Fulbright & Jaworski L.L.P.

(57) ABSTRACT

Prosthetic implants designed to be implanted in the cornea for modifying the cornea curvature and altering the corneal refractive power for correcting myopia, hyperopia, astigmatism, and presbyopia, and, in addition, such implants formed of a micro-porous hydrogel material.

8 Claims, 6 Drawing Sheets

CORNEAL IMPLANT AND METHOD OF MANUFACTURE

RELATED APPLICATIONS

This application is a divisional of U.S. patent application Ser. No. 09/385,103, filed Aug. 27, 1999, now U.S. Pat. No. 6,361,560, which is a continuation-in-part of U.S. patent application Ser. No. 09/219,594, filed Dec. 23, 1998, now U.S. Pat. No. 6,102,946.

FIELD OF THE INVENTION

The field of this invention relates to prosthetic implants designed to be implanted in the cornea for modifying the cornea curvature and altering the corneal refractive power for correcting myopia, hyperopia, astigmatism, and presbyopia, and, in addition, to such implants formed of a micro-porous hydrogel material.

BACKGROUND OF THE INVENTION

It is well known that anomalies in the shape of the eye can be the cause of visual disorders. Normal vision occurs when light that passes through and is refracted by the cornea, the lens, and other portions of the eye, and converges at or near the retina. Myopia or near-sightedness occurs when the light converges at a point before it reaches the retina and, conversely, hyperopia or far-sightedness occurs when the light converges a point beyond the retina. Other abnormal conditions include astigmatism where the outer surface of the cornea is irregular in shape and effects the ability of light to be refracted by the cornea. In addition, in patients who are older, a condition called presbyopia occurs in which there is a diminished power of accommodation of the natural lens resulting from the loss of elasticity of the lens, typically becoming significant after the age of 45.

Corrections for these conditions through the use of implants within the body of the cornea have been suggested. Various designs for such implants include solid and split-ring shaped, circular flexible body members and other types of ring-shaped devices that are adjustable. These implants are inserted within the body of the cornea for changing the shape of the cornea, thereby altering the its refractive power.

These types of prostheses typically are implanted by first making a tunnel and/or pocket within the cornea which leaves the Bowman's membrane intact and hence does not relieve the inherent natural tension of the membrane.

In the case of hyperopia, the corneal curvature must be steepened, and in the correction of myopia, it must be flattened. The correction of astigmatism can be done by flattening or steepening various portions of the cornea to correct the irregular shape of the outer surface. Bi-focal implants can be used to correct for presbyopia.

It has been recognized that desirable materials for these types of prostheses include various types of hydrogels. Hydrogels are considered desirable because they are hydrophilic in nature and have the ability to transmitting fluid through the material. It has been accepted that this transmission of fluid also operates to transmit nutrients from the distal surface of the implant to the proximal surface for providing proper nourishment to the tissue in the outer portion of the cornea.

However, while hydrogel lenses do operate to provide fluid transfer through the materials, it has been found that nutrient transfer is problematic because of the nature of fluid transfer from cell-to-cell within the material. Nutrients do not pass through the hydrogel material with the same level of efficacy as water. Without the proper transfer of nutrients, tissue in the outer portion of the cornea will die causing further deterioration in a patient's eyesight.

Thus, there is believed to be a demonstrated need for a material for corneal implants that will allow for the efficacious transmission of nutrients from the inner surface of a corneal implant to the outer surface, so that tissue in the outer portion of the cornea is properly nourished. There is also a need for a more effective corneal implant for solving the problems discussed above.

DESCRIPTION OF THE PRIOR ART

SUMMARY OF THE INVENTION

The present invention is directed to a corneal implant formed of a biocompatible, permeable, micro-porous hydrogel with a refractive index substantially similar to the refractive index of the cornea. The device, when placed under a lamellar dissection made in the cornea (such as a corneal flap), to relieve tension of Bowman's membrane, alters the outer surface of the cornea to correct the refractive error of the eye. By relieving the pressure and subsequent implantation of the device, the pressure points which typically are generated in present corneal surgeries are eliminated, and hence reduced risk to patients of extrusion of implants.

The implant is preferably generally circular in shape and is of a size greater than the size of the pupil in normal or bright light, and can specifically be used to correct hyperopia, myopia, astigmatism, and/or presbyopia. Due to the complete non-elastic nature of the corneal tissue, it is necessary to place the implant in the cornea with Bowman's membrane compromised, such as through a corneal lamellar dissection, to prevent extrusion of the implant from the cornea over the lifetime of the implant. Extrusion is undesirable because it tends to cause clinical complications and product failure.

Preferably, for the correction of hyperopia, the implant is formed into a meniscus-shaped disc with its anterior surface radius smaller (steeper) than the posterior surface radius, and with negligible edge thickness. This design results in a device that has a thickness or dimension between the anterior and posterior surfaces along the central axis greater than at its periphery. When such an implant is placed under the corneal flap, the optical zone of the cornea is steepened and a positive optical power addition is achieved.

For the correction of myopia, the implant is shaped into a meniscus lens with an anterior surface curvature that is flatter than the posterior surface. When the implant is placed concentrically on the stromal bed the curvature of the anterior surface of the cornea in the optic zone is flattened to the extent appropriate to achieve the desired refractive correction.

For astigmatic eyes, implants are fabricated with a cylindrical addition along one of the axes. This device can be oval or elliptical in shape, with a longer axis either in the direction of cylindrical power addition or perpendicular to it. The implant preferably has a pair of markers such as, for example, protrusions, indentations or other types of visual indicators, in the direction of the cylindrical axis to easily mark and identify this direction. This indexing assists the surgeon in the proper placement of the implant under the flap with the correct orientation during surgery to correct astigmatism in any axis.

For simple or compound presbyopia, the implant is made by modifying the radius of curvature in the central 1.5–3 mm, thereby forming a multi-focal outer corneal surface where the central portion of the cornea achieves an added plus power for close-up work. The base of an implant designed for compound presbyopia can have a design to alter the cornea to achieve any desired correction for the myopic, hyperopic, or astigmatic eye.

The material from which any one or more of these implants are made is preferably a clear, permeably, microporous hydrogel with a water content greater than 40% up to approximately 90%. The refractive index should be substantially identical to the refractive index of corneal tissue. The permeability of the material is effected through a network of irregular passageways such as to permit adequate nutrient and fluid transfer to prevent tissue necrosis, but which are small enough to act as a barrier against the tissue ingrowth from one side of the implant to another. This helps the transmembrane tissue viability while continuing to make the implant removable and exchangeable.

The refractive index of the implant material should be in the range of 1.36–1.39, which is substantially similar to that of the cornea (1.376). This substantially similar refractive index prevents optical aberrations due to edge effects at the cornea-implant interface.

The microporous hydrogel material can be formed from at least one (and preferably more) hydrophilic monomer, which is polymerized and cross-linked with at least one multi- or di-olefinic cross-linking agent.

The implants described above can be placed in the cornea by making a substantially circular lamellar flap using any commercially available microkeratome. When the flap is formed, a hinge is preferably left to facilitate proper alignment of the dissected corneal tissue after the implant is placed on the exposed cornea.

The implants described above which can be used for correcting hyperopia or hyperopia with astigmatism are preferably made into a disc shape that is nominally about 4.5 mm in diameter and bi-meniscus in shape. The center of the lens is preferably no greater than 50 micrometers thick. The edge thickness should be less than two keratocytes (i.e., about 15 micrometers).

An improvement over the lenses described above for correcting myopia with astigmatism includes forming a lens in the shape of a ring with one or more portions in the center being solid and defining voids in the center section for shaping the astigmatic component by providing solid portions under the flatter meridian of the astigmatic myopic eye. An example of such a shape includes a ring with a rib extending across the center that is either squared off or rounded where it contacts the ring. Another example is a ring with one or more quadrants filled in, with the other ones forming voids. Other shapes can used to provide a solid portion under the flatter meridan.

BRIEF DESCRIPTION OF THE DRAWINGS

A better understanding of the invention can be obtained from the detailed description of exemplary embodiments set forth below, when considered in conjunction with the appended drawings, in which.

DETAILED DESCRIPTION OF EXEMPLARY EMBODIMENTS

Figure 1:
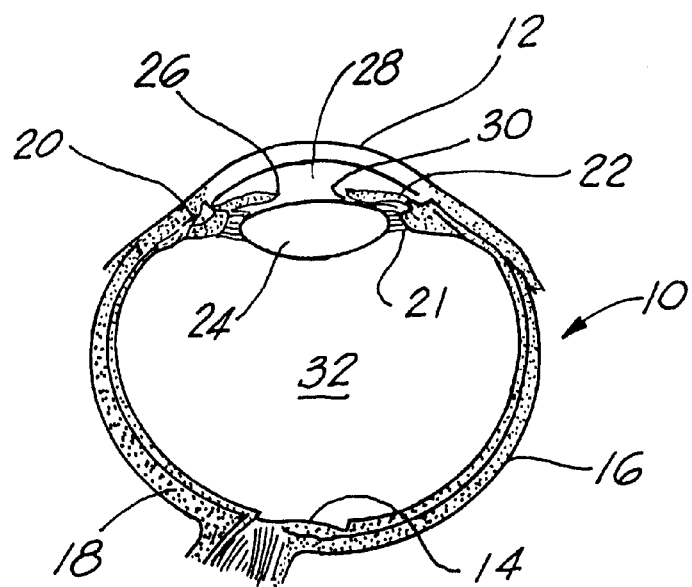
FIG. 1 is a schematic illustration of a horizontal section of a human eye.

Referring first to FIG. 1 of the drawings, a schematic representation of the globe of the eye 10 is shown, which resembles a sphere with an anterior, bulged spherical portion 12 that represents the cornea. The eye 10 is made up of three concentric coverings that enclose the various transparent media through which light must pass before reaching the light sensitive retina 14.

The outer-most covering is a fibrous protective portion that includes a posterior layer which is white and opaque, called the sciera 16, which is sometimes referred to as the white of the eye where it is visible from the front. The anterior 1/6th of this outer layer is the transparent cornea 12.

A middle covering is mainly vascular and nutritive in function and is made up of the choroid 18, the ciliary 20 and the iris 22. The choroid generally functions to maintain the retina. The ciliary muscle 21 is involved in suspending the lens 24 and accommodating the lens. The iris 22 is the most anterior portion of the middle covering of the eye and is arranged in a frontal plane. The iris is a thin circular disc corresponding to the diaphragm of a camera, and is perforated near its center by a circular aperture called the pupil 26. The size of the pupil varies to regulate the amount of light that reaches the retina 14. It contracts also to accommodate, which serves to sharpen the focus by diminishing spherical aberrations. The iris 22 divides the space between the cornea 12 and the lens 24 into an anterior chamber 28 and posterior chamber 30.

The inner-most covering is the retina 14, consisting of nerve elements which form the true receptive portion for visual impressions that are transmitted to the brain. The vitreous 32 is a transparent gelatinous mass which fills the posterior 4/5ths the globe 10. The vitreous supports the ciliary body 20 and the retina 14.

Figure 2:
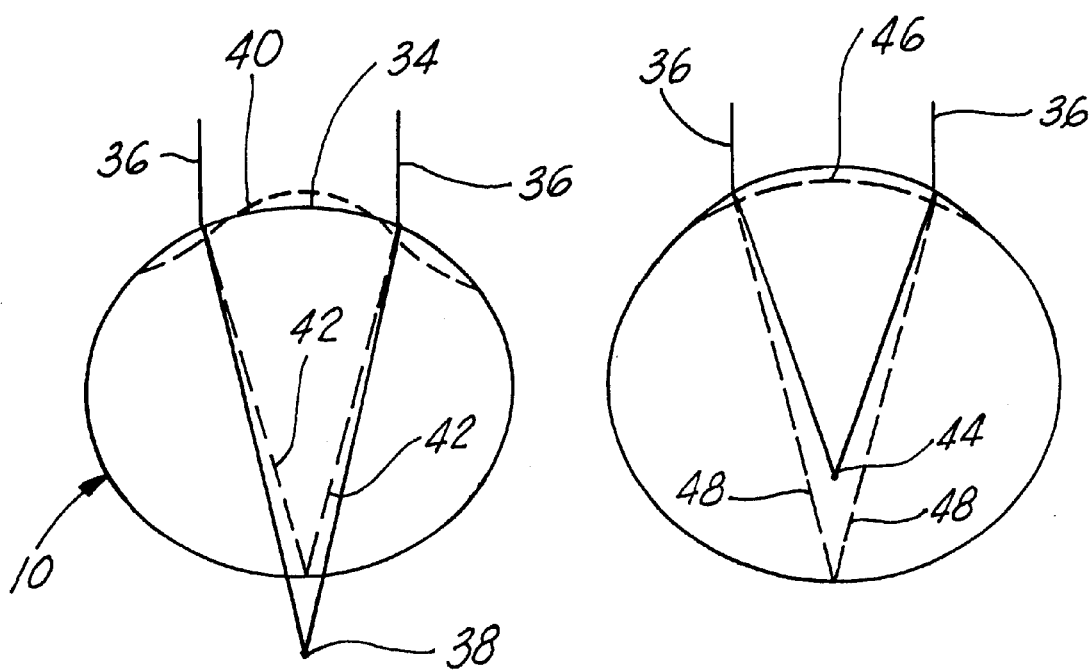
FIG. 2 is a schematic illustration of an eye system showing adjustment of the cornea to steepen the corneal slope to correct for hyperopia.

Referring to FIG. 2 of the drawings, the globe of an eye 10 is shown as having a cornea 12 with a normal curvature represented by a solid line 34. For people with normal vision, when parallel rays of light 36 pass through the corneal surface 34, they are refracted by the corneal surfaces to converge eventually near the retina 14 (FIG. 1). The diagram of FIG. 2 discounts, for the purposes of this discussion, the refractive effect of the lens or other portions of the eye. However, as depicted in FIG. 2, when the eye is hyperopic the rays of light 36 are refracted to converge at a point 38 behind the retina.

If the outer surface of the cornea 12 is caused to steepen, as shown by dotted lines 40, such as through the implantation of a corneal implant of an appropriate shape as discussed below, the rays of light 36 are refracted from the steeper surface at a greater angle as shown by dotted lines 42, causing the light to focus at a shorter distance, such as directly on the retina 14.

Figure 3:
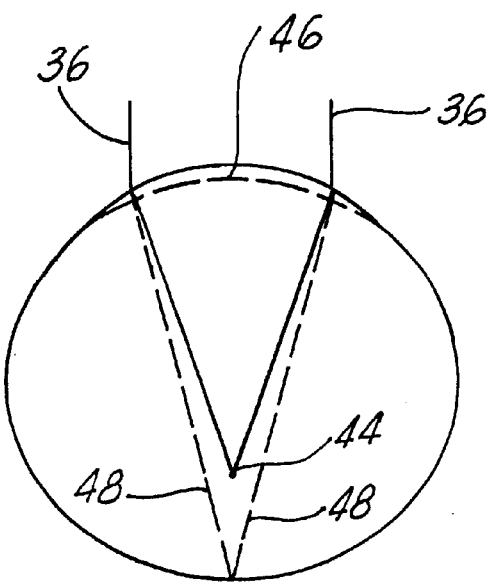
FIG. 3 is a schematic illustration of an eye system showing adjustment of the cornea to flatten the corneal slope to correct for myopia.

FIG. 3 shows a similar eye system to that of FIG. 2 except that the normal corneal curvature causes the light rays 36 to focus at a point 44 in the vitreous which is short of the retinal surface. This is typical of a myopic eye. If the cornea is flattened as shown by dotted lines 46 through the use of a properly-shaped corneal implant, light rays 36 will be refracted at a smaller angle and converge at a more distant point such as directly on the retina 14 as shown by dotted lines 48.

Figure 4A:
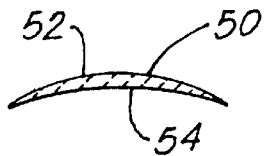
FIGS. 4a and 4b are sectional and plan views of a solid corneal implant for correcting hyperopia.
Figure 4B:
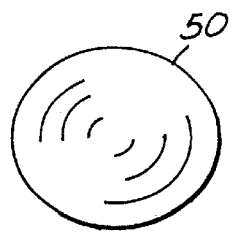

A hyperopic eye of the type shown in FIG. 2 can be corrected by implanting an implant 50 having a shape as shown in FIGS. 4a, 4b. The implant 50 is in the shape of a meniscus lens with an outer surface 52 that has a radius of curvature that is smaller than the radius of curvature of the inner surface 54. When a lens of this type is implanted using the method discussed below, it will cause the outer surface of the cornea to become steeper in shape as shown by reference numeral 40 in FIG. 2, correcting the patient's vision so that light entering the eye will converge on the retina as shown by the dotted lines 42 in FIG. 2.

The lens 50 shown in FIGS. 4a and 4b is formed with a bi-meniscus shape, with the anterior and posterior surfaces having different radii of curvature. The anterior surface has a greater radius than the posterior surface. The lens 50 preferably has a nominal diameter of about 4.5 mm. The center of the lens is preferably no greater than 50 micrometers thick to enhance the diffusion characteristics of the material from which the lens is formed, which allows for more effective transmission of nutrients through the lens material and promotes better health of the anterior corneal tissue. The outer edge of the lens 50 has a thickness that is less than the dimensions of two keratocytes (i.e., about 15 micrometers) juxtaposed side-by-side, which are the fixed flattened connective tissue cells between the lamellae of the cornea. An edge thickness as specified prevents stacking and recruitment of keratocytes in the lens material so that keratocyte stacking and recruitment does not take place. This in turn eliminates unorganized collagen that forms undesirable scar tissue and infiltrates the lens, which tends to compromise the efficacy of the lens.

On the other hand, in order to cure myopia, an implant 56 having the shape shown in FIGS. 5a, 5b, can be used where an outer surface 58 is flatter or formed with a larger radius than that of the inner surface 60 which is formed with a radius of curvature substantially identical to that of the corneal stroma bed generated by the lamellar dissection described below. The implant 56 has a transition zone 62 formed between the outer and inner surfaces 58, 60, which is outside of the optical zone. In this way, the curvature of the outer surface of the cornea, as shown in FIG. 3, is flattened to an extent appropriate to achieve the proper refractive correction desired so that light entering the eye will converge on the retina as shown in FIG. 3.

Figure 5A:
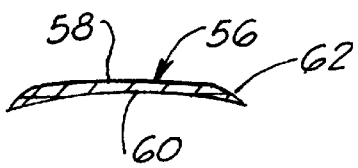
FIGS. 5a and 5b are sectional and plan views of a solid corneal implant for correcting myopia.
Figure 5B:
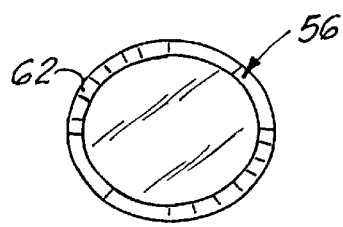
Figure 6A:
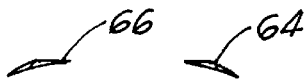
FIGS. 6a and 6b are sectional and plan views of ring-shaped corneal implant for correcting myopia.
Figure 6B:
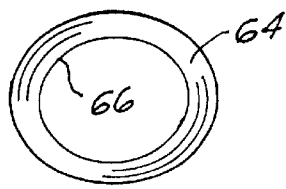

Alternatively, instead of using a solid implant as shown in FIGS. 5a, 5b, for correcting myopia, a ring 64 of the type shown in FIGS. 6a, 6b could be used. This ring has substantially the same effect as the implant shown in FIGS. 5a, 5b, by flattening the outer surface of the cornea shown in FIG. 3. The ring 64 has a center opening 66 that is preferably larger than the optical zone so as not to cause spherical aberrations in light entering the eye.

Figure 7A:
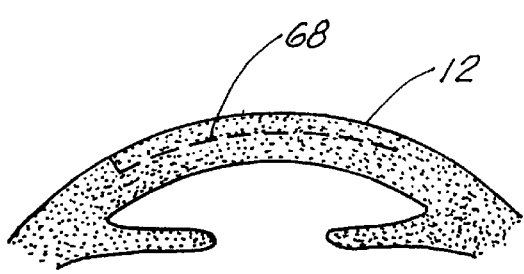
FIGS. 7a and 7b are schematic representations of a lamellar dissectomy, with FIG. 7b showing in particular the portion of the dissected cornea being connected through a hinge to the intact cornea.
Figure 7B:
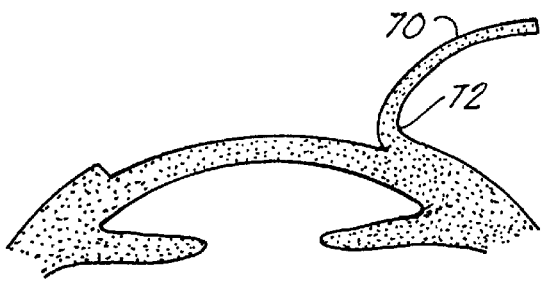

Implants of the type shown in FIGS. 4, 5 and 6 can be implanted in the cornea using a lamellar dissectomy shown schematically in FIGS. 7a, 7b. In this procedure, a keratome (not shown) is used in a known way to cut a portion of the outer surface of the cornea 12 along dotted lines 68 as shown in FIG. 7a. This type of cut is used to form a corneal flap 70 shown in FIG. 7b, which remains attached to the cornea 12 through what is called a hinge 72. The hinge 72 is useful for allowing the flap 70 to be replaced with the same orientation as before the cut.

Figure 8:
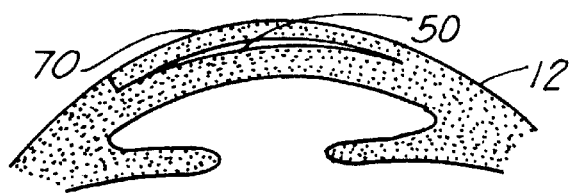
FIG. 8 is a schematic representations of a cornea in which an implant has been implanted for a hyperopic correction.
Figure 9:
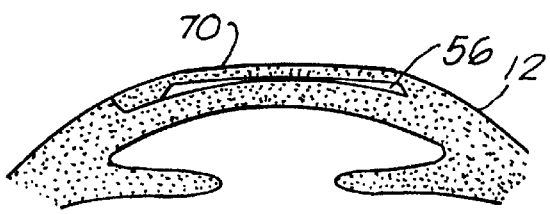
FIGS. 9 and 10 are schematic representations of a cornea in which solid and ring-shaped implants, respectively, have been implanted lamellar for a myopic correction.
Figure 10:
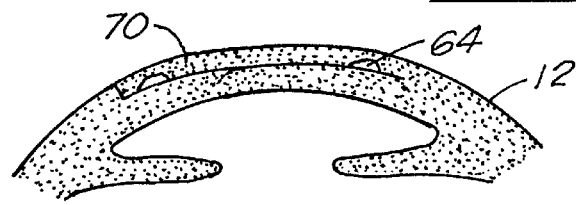
Figure 11A:
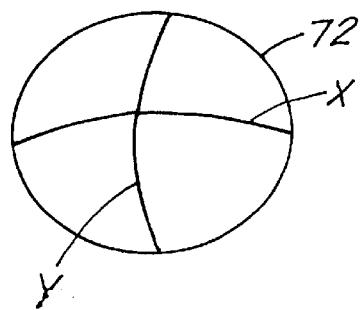
FIGS. 11a, 11b, and 11c are plan and sectional views of an implant useful for correcting astigmatism where two axes have different diopter powers.
Figure 12A:
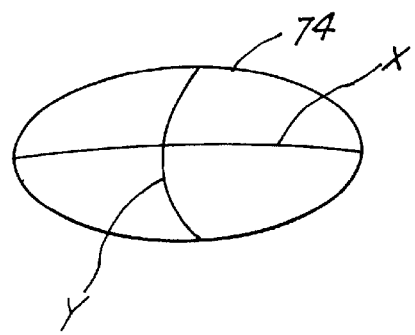
FIGS. 12a, 12b, and 12c are plan and sectional views of an second implant for correcting astigmatism where the implant is elliptical in shape.
Figure 11B:
Figure 12B:
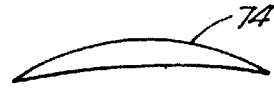
Figure 11C:
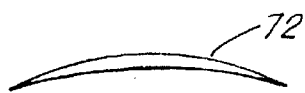
Figure 12C:
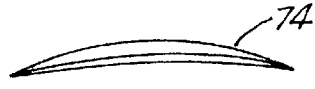
Figure 13:
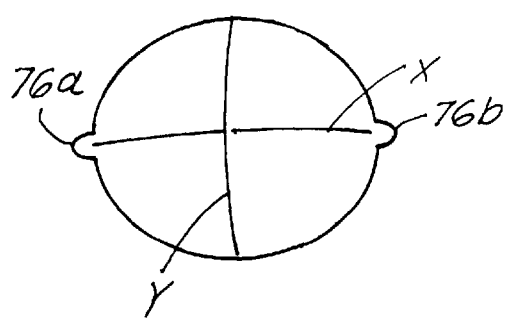
FIG. 13 is a plan view of an implant with a pair of tabs used to identify an axis for astigmatic correction.
Figure 14:
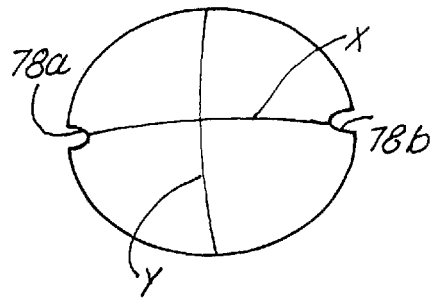
FIG. 14 is a plan view of a second implant for astigmatic correction where indentations are used instead of tabs.

As is also known in the art, the flap is cut deeply enough to dissect the Bowman's membrane portion of the cornea, such as in keratome surgery or for subsequent removal of the tissue by laser or surgical removal. A corneal flap of 100 to 200 microns, typically 160 to 180 microns, will be made to eliminate the Bowman's membrane tension. This reduces the possibility of extrusion of the implants due to pressure generated within the cornea caused by the addition of the implant. Implants of the type shown in FIGS. 4, 5 and 6 are shown implanted in corneas in FIGS. 8, 9 and 10, respectively, after the flap has been replaced in its normal position. These figures show the corrected shape for the outer surface of the cornea as a result of implants of the shapes described.

Implants can also be formed with a cylindrical addition in one axis of the lens in order to correct for astigmatism, as shown in the implants in FIGS. 11–16. Such implants can be oval or elliptical in shape, which the longer axis either in the direction of cylindrical power addition or perpendicular to it. For example, the implant can be circular as shown in FIG. 11a where the implant 72 has axes identified as x, y. In the case of a circular implant 72, the axes of the implant have different diopter powers as shown in FIGS. 11b and 11bc, which are cross-sectional views of the implant 72 along the x and y axes, respectively. The different thicknesses of the lenses in FIGS. 11b and 11c illustrate the different diopter powers along these axes.

Alternatively, as shown in FIG. 5a, an astigmatic implant 74 can be oval or elliptical in shape. The implant 74 also has axes x, y. As shown in the cross-sectional views of the implant 74 in FIGS. 12b, 12c, along those two axes, respectively, the implant has different diopter powers as shown by the different thicknesses in the figures.

Figure 15:
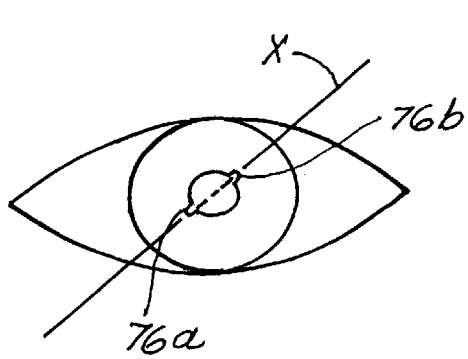
FIGS. 15 and 16 are schematic representations showing implants with tabs orientated along the astigmatic axis for correcting astigmatism.
Figure 16:
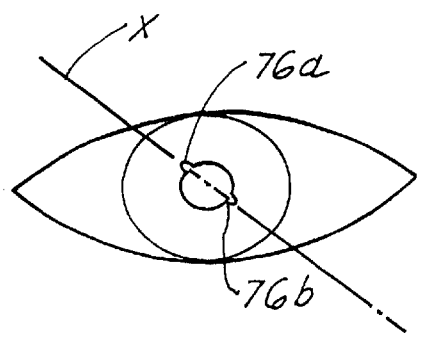
Figure 17:
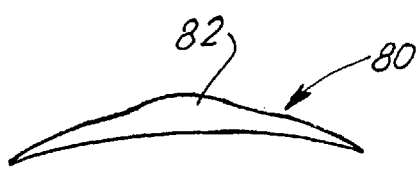
FIG. 17 is a sectional view of a corneal implant shaped to correct for compound presbyopia with an additional power in the center of an implant for correcting hyperopia.
Figure 18:
FIG. 18 is a sectional view of another corneal implant shaped to correct for compound presbyopia with additional power in the center of an implant for correcting myopia.
Figure 19:
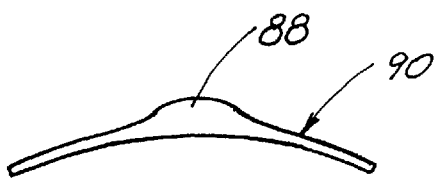
FIG. 19 is a sectional view of a corneal implant with additional power in the center for correcting simple presbyopia.

Because implants of the type identified by reference numeral 72, 74 are relatively small and transparent, it is difficult for the surgeon to maintain proper orientation along the x and y axes. In order to assist the surgeon, tabs 76a, 76b or indentations 78a, 78b are used to identify one or the other of the axis of the implant to maintain proper alignment during implantation. This is shown in FIGS. 15, 16 where, for example, indentations 76a, 76b, are aligned with axis x which has been determined as the proper axis for alignment in order to effect the astigmatic correction. Alternatively, other types of markers could be used such as visual indicators such as markings on or in the implants outside of the optical zone. Referring to FIGS. 17–21, implants with presbyopic corrections are shown. In FIG. 17, an compound implant 80 is shown, which is appropriate for hyperopic correction, which has an additional power section 82 in the center. As shown, the implant 82 has anterior and posterior curvatures similar to those in FIGS. 4a, 4b, in order to correct for hyperopia. In FIG. 18, a central power add 84 is formed on another compound implant 86, which has a base shape similar to the one shown in FIGS. 5a, 5b, and is appropriate for a myopic correction. In FIG. 19, a central power portion 88 is added to an simple planal implant 90 which has outer and inner surfaces of equal radii, which does not add any correction other than the central power.

Figure 20A:
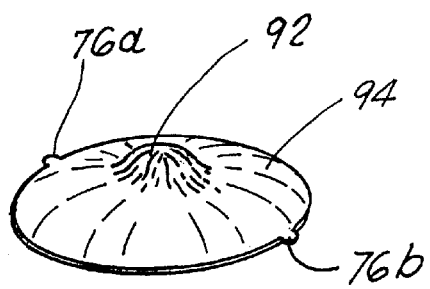
FIG. 20a is a schematic representation of a corneal implant for an astigmatic correction with a central power add for correcting presbyopia, showing in particular a pair of tabs for proper alignment of the lens.

The central power add portions 82, 84, and 88 are preferably within the range of 1.5–3 mm in diameter, most preferably 2 mm, and which provide a multi-focal outer corneal surface where the central portion of the cornea achieves an added plus power for close-up work. In addition to the based device having no correction, or corrections for hyperopia or myopia, the base device can have a simple spherical correction for astigmatism as shown in FIG. 20a, where a central power add 92 is added to an implant 94 similar to the one shown in FIG. 11a, which also includes tabs 76a, 76b.

Figure 20B:
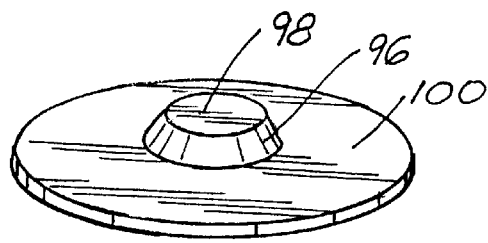
FIG. 20b is a schematic representation of a another corneal implant with a center power add for non-astigmatic correction, which shows in particular a steep transition between the central add and the remainder of the implant.

As shown in FIG. 20b in order to enhance the acuity of a presbyopic implant, a transition zone 96 can be formed around the central power add 98 for implant 100. This transition zone 96 is a sharp zone change in power from central added power to peripheral base power and is anchored over a radial distance 0.5 to 0.2 mm start to from the end of the central zone.

Figure 21A:
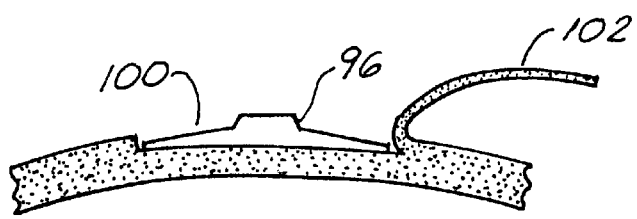
FIGS. 21a and 21b are schematic representations showing the use of a lamellar dissection for implanting a lens of the type shown in FIG. 20b.
Figure 21B:
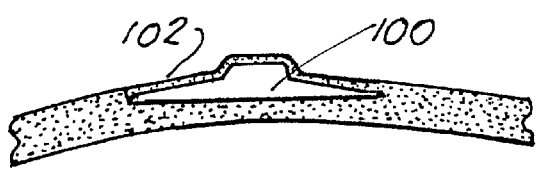

Implantation of the device shown in FIG. 20b, is illustrated in FIGS. 21a, 21b, where a flap 102 formed through a lamellar dissectomy is shown pulled back in FIG. 21a so that the implant 100 can be positioned, and then replaced as shown in FIG. 21b for the presbyopic correction. As shown, the formation of a sharp transition 96 on the implant 100 provides a well defined central power after implantation is complete.

Figure 22:
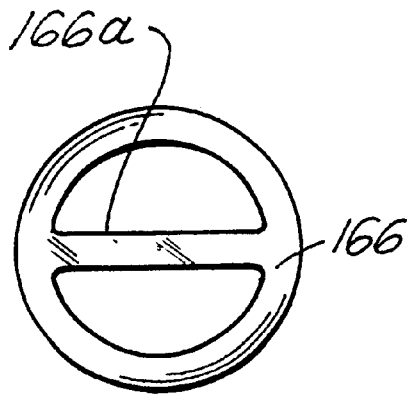
FIGS. 22 and 23 are schematic representations of several lenses useful for correcting myopia with astigmatism formed in the shape of a ring with a rib extending across the center of the lens.
Figure 23:
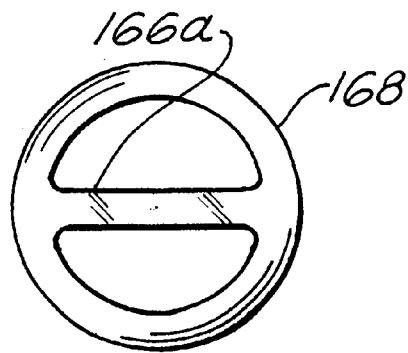

FIGS. 22 and 23 illustrate lenses 166, 168, respectively, which are useful for correcting myopia with astigmatism. As shown, these lenses are ring-shaped, similar to the one in FIGS. 6a, 6b. However, the lenses 166,168 include rib sections 166a, 168a, respectively, which extend across the center of each lens and define voids between the ribs and the outer periphery of the lenses. These solid rib sections shape the astigmatic component by providing solid portions under the flatter meridian of the astigmatic myopic eye, when these flatter portions are located above the ribs. The ribs 166a, 168a can be formed in any suitable shape such as, by way of example, the rib 166a being squared off as shown in FIG. 22 or the rib 168a being rounded s shown in FIG. 23, where they contact their respective rings.

Figure 24:
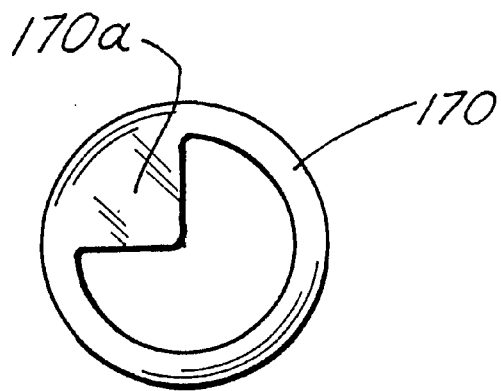
FIG. 24 is another schematic representation of another lens for correcting myopia with astigmatism where the ring-shaped lens has one quadrant that is solid, while the rest of the center portion forms a void.

Another example of a design for correcting myopia with astigmatism is a lens 170 as shown in FIG. 24, which is also ring-shaped but has one its quadrants 170a filled in. This lens can be used where the flatter portion of an astigmatic eye is located in a position where the quadrant can be located beneath the flatter portion. The solid portion of the lens will tend to raise the flattened portion so that a smooth rounded outer surface is formed. As can readily be appreciated, lenses can be formed with solid portions located in any number of places where they can positioned under the flattened portion of an astigmatic eye to achieve the same end.

The implants described above are preferably formed of a microporous hydrogel material in order to provide for the efficacious transmission of nutrients from the inner to the outer surface of the implants. The hydrogels also preferably have micropores in the form of irregular passageways, which are small enough to screen against tissue ingrowth, but large enough to allow for nutrients to be transmitted. These microporous hydrogels are different from non-microporous hydrogels because they allow fluid containing nutrients to be transmitted between the cells that make up the material, not from cell-to-cell such as in normal hydrogel materials. Hydrogels of this type can be formed from at least one, and preferably more, hydrophillic monomer which is polymerized and cross-linked with at least one multi-or di-olefinic cross-linking agent.

An important aspect of the materials of the present invention is that the microporous hydrogel have micropores in the hydrogel. Such micropores should in general have a diameter ranging from 50 Angstroms to 10 microns, more particularly ranging from 50 Angstroms to 1 micron. A microporous hydrogel in accordance with the present invention can be made from any of the following methods.

Hydrogels can be synthesized as a zero gel by ultraviolet or thermal curing of hydrophillic monomers and low levels of cross-linking agents such as diacrylates and other UV or thermal initiators. These lightly cross-linked hydrogels are then machined into appropriate physical dimensions and hydrated in water at elevated temperatures. Upon complete hydration, hydrogel prosthesis are flash-frozen to temperatures below negative 40° C., and then gradually warmed to a temperature of negative 20° C. to negative 10° C. and maintained at the same temperature for some time, typically 12 to 48 hours, in order to grow ice crystals to larger dimensions to generate the porous structure via expanding ice crystals. The frozen and annealed hydrogel is then quickly thawed to yield the microporous hydrogel device. Alternatively, the hydrated hydrogel device can be lyophilized and rehydrated to yield a microporous hydrogel.

Still further, the microporous hydrogel can also be made by starting with a known formulation of monomers which can yield a desired cross-linked hydrogel, dissolving in said monomer mixture a low molecular weight polymer as a filler which is soluble in said mixture and then polymerizing the mixture. Resulted polymer is converted into the required device shape and then extracted with an appropriate solvent to extract out the filled polymer and the result in a matrix hydrated to yield a microporous device.

Still further and alternatively, microporous hydrogels can also be made by any of the above methods with the modification of adding an adequate amount of solvent or water to give a pre-swollen finished hydrogel, which can then be purified by extraction. Such formulation can be directly cast molded in a desired configuration and do not require subsequent machining processes for converting.

I claim:

1. A corneal implant, comprising:
   a) a body formed of an optically clear, biocompatible material having inner and outer surfaces and an index of refraction substantially the same as that of corneal tissue;
   b) the body being solid and formed of a microporous hydrogel having irregular passageways for nutrient transport, the microporous hydrogel having micropores ranging in diameter from 50 Angstroms to 10 microns.

2. The corneal implant of claim 1, wherein the body is shaped to correct for hyperopia.

3. The corneal implant of claim 1, wherein the body is shaped to correct for myopia.

4. The corneal implant of claim 1, wherein the implant is shaped to correct for astigmatism.

5. The corneal implant of claim 1, wherein the implant is shaped to correct for presbyopia.

6. The corneal implant of claim 1, wherein the microporous hydrogel has a water content greater than 40% and up to approximately 90%.

7. The corneal implant of claim 1, wherein the microporous hydrogel is formed from at least one hydrophilic monomer which is cross-linked with at least one multi- or di-olefinic cross-linking agent.

8. The corneal implant of claim 1, wherein the micropores are formed to permit nutrient and fluid transfer to prevent tissue necrosis, and the micropores are sized to act as a barrier against tissue in growth.

* * * * *